(12) United States Patent
Kim et al.

(10) Patent No.: US 10,561,413 B1
(45) Date of Patent: Feb. 18, 2020

(54) SUTURING NEEDLE FOR INJECTING GOLD THREAD FOR USE OF HAIR LOSS TREATMENT

(71) Applicants: Jong Hwan Kim, Seoul (KR); Woo Tae Kim, Seoul (KR)

(72) Inventors: Jong Hwan Kim, Seoul (KR); Woo Tae Kim, Seoul (KR)

( * ) Notice: Subject to any disclaimer, the term of this patent is extended or adjusted under 35 U.S.C. 154(b) by 0 days.

(21) Appl. No.: 16/192,331

(22) Filed: Nov. 15, 2018

(30) Foreign Application Priority Data

Aug. 13, 2018 (KR) ........................ 10-2018-0094372

(51) Int. Cl.
*A61B 17/06* (2006.01)
*A61L 31/02* (2006.01)
(Continued)

(52) U.S. Cl.
CPC .. *A61B 17/06066* (2013.01); *A61B 17/06166* (2013.01); *A61K 9/70* (2013.01);
(Continued)

(58) Field of Classification Search
CPC ........ A61B 17/06066; A61B 17/06004; A61B 17/06119; A61B 17/06142; A61B 2017/00349; A61B 2017/06071; A61B 2017/06076; A61B 2017/0608; A61B 2017/06085; A61B 2017/0609; A61B 2017/06095; A61B 2017/061; A61N 17/06004; A61N 17/06066; A61N 17/06166; A61K 9/10; A61L 31/022; A61L 31/16
See application file for complete search history.

(56) References Cited

U.S. PATENT DOCUMENTS

| 312,408 | A | * | 2/1885 | Wackerhagen | .. A61B 17/06066 606/223 |
| 527,263 | A | * | 10/1894 | Blanchard | ........ A61B 17/06066 606/223 |

(Continued)

FOREIGN PATENT DOCUMENTS

| DE | 3639489 A1 * | 5/1988 | ....... A61B 17/06004 |
| EP | 1726317 A1 | 11/2006 | |

(Continued)

OTHER PUBLICATIONS

Chan, et al., English language machine translation of KR 10-1748755.
(Continued)

*Primary Examiner* — Laura A Bouchelle
*Assistant Examiner* — Mark A Igel
(74) *Attorney, Agent, or Firm* — Innovation Capital Law Group, LLP; Vic Lin

(57) ABSTRACT

A suturing needle is provided for injecting a gold thread. The suturing needle includes a needle body having a sharpened tip part at an upper end thereof. In addition, the suturing needle includes an upper groove provided on the sharpened tip part to hold the gold thread therein, and a lower groove provided near a lower end of the needle body to be opposite to the upper groove. Also, the suturing needle includes a handle part detachably combined with the lower end of the needle body. Various embodiments are possible.

8 Claims, 9 Drawing Sheets

(51) Int. Cl.
*A61L 31/16* (2006.01)
*A61K 33/24* (2019.01)
*A61B 17/00* (2006.01)
*A61K 9/70* (2006.01)

(52) U.S. Cl.
CPC ............ *A61K 33/24* (2013.01); *A61L 31/022* (2013.01); *A61L 31/16* (2013.01); *A61B 2017/00747* (2013.01); *A61B 2017/00862* (2013.01); *A61B 2017/00893* (2013.01); *A61B 2017/06171* (2013.01)

(56) References Cited

U.S. PATENT DOCUMENTS

| | | | | | |
|---|---|---|---|---|---|
| 856,686 | A * | 6/1907 | Edwards | .......... | A61B 17/06004 606/225 |
| 879,758 | A * | 2/1908 | Foster | .............. | A61B 17/06004 606/225 |
| 965,219 | A * | 7/1910 | Nyborg | ............ | A61B 17/06004 606/225 |
| 1,122,210 | A * | 12/1914 | Lukens | ............ | A61B 17/06004 606/226 |
| 1,131,155 | A * | 3/1915 | Murphy | ........... | A61B 17/06004 606/225 |
| 1,678,361 | A * | 7/1928 | Shearon | ........... | A61B 17/06004 403/59 |
| 3,265,070 | A * | 8/1966 | Kurtz | .................... | A61B 17/06 606/223 |
| 3,892,240 | A * | 7/1975 | Park | ................ | A61B 17/06004 606/225 |
| 4,221,212 | A * | 9/1980 | Miller | ....................... | A61F 2/10 606/187 |
| 4,378,019 | A * | 3/1983 | Yamada | .................... | A61F 2/10 606/187 |
| 4,382,444 | A * | 5/1983 | Malmin | ................. | A61B 17/06 606/187 |
| 4,457,128 | A * | 7/1984 | Brunvoll | .......... | A61B 17/06004 57/23 |
| 4,583,540 | A * | 4/1986 | Malmin | ................. | A61B 17/06 606/103 |
| 5,312,422 | A * | 5/1994 | Trott | .................. | A61B 17/0469 604/272 |
| 6,059,807 | A * | 5/2000 | Boudjema | .......... | A61B 10/0096 606/185 |
| 6,641,596 | B1 * | 11/2003 | Lizardi | .............. | A61B 17/0401 606/232 |
| 2003/0141268 | A1 * | 7/2003 | Kerns | .................... | A61J 11/004 215/11.1 |
| 2004/0243135 | A1 * | 12/2004 | Koseki | .............. | A61B 17/0485 606/80 |
| 2004/0267314 | A1 * | 12/2004 | Wolf | ....................... | A61B 17/04 606/230 |
| 2006/0036265 | A1 * | 2/2006 | Dant | .................. | A61B 17/0469 606/144 |
| 2007/0162054 | A1 * | 7/2007 | Horaguchi | ......... | A61B 17/0401 606/148 |
| 2012/0101522 | A1 * | 4/2012 | Megaro | ............ | A61B 17/06109 606/228 |
| 2014/0135802 | A1 * | 5/2014 | Mantovani | ......... | A61B 17/0482 606/144 |
| 2016/0331371 | A1 * | 11/2016 | Kim | ................. | A61B 17/06004 |

FOREIGN PATENT DOCUMENTS

| | | | | |
|---|---|---|---|---|
| FR | 2854051 A1 * | 10/2004 | ....... | A61B 17/06066 |
| JP | 4987149 B1 | 7/2012 | | |
| KR | 20120072295 A | 7/2012 | | |
| KR | 20150145578 A | 12/2015 | | |
| KR | 20160074933 A | 6/2016 | | |
| KR | 10-1696855 B1 | 1/2017 | | |
| KR | 101696855 B1 | 1/2017 | | |
| KR | 10-1748755 B1 | 6/2017 | | |
| KR | 101748755 B1 | 6/2017 | | |

OTHER PUBLICATIONS

Kim, et al., English language machine translation of KR 10-1696855.

* cited by examiner

SUTURING NEEDLE FOR INJECTING GOLD THREAD FOR USE OF HAIR LOSS TREATMENT

CROSS-REFERENCE TO RELATED APPLICATION(S)

This application is based on and claims priority under 35 U.S.C. § 119 to Korean Patent Application No. 10-2018-0094372, filed on Aug. 13, 2018, in the Korean Intellectual Property Office, the disclosure of which is incorporated by reference herein in its entirety.

TECHNICAL FIELD

The present disclosure relates to a suturing needle for injecting a gold thread. Particularly, the present disclosure relates to a suturing needle capable of accurately and easily injecting a gold thread into a treatment area of scalp for a hair loss treatment and preventing the injected gold thread from separating from the treatment area.

BACKGROUND

It is generally known that the human body has self-healing ability, i.e., the ability to spontaneously cure diseases, as well as the resistance against various kinds of diseases. The self-healing ability occurs naturally in the human body to keep healthy. For example, where there is a fever due to cold or body aches, the sweat pores are open and the sweat is ejected to lower the body temperature. In another example, in case of eating spoiled food or excessively drinking, it may cause vomiting to protect the body.

There is also a self-healing substance in the subcutaneous layer of the human body. For example, when a foreign substance enters the subcutaneous layer, the self-healing substances are generated and surround the foreign substance to protect the subcutaneous tissue from the foreign substance. As a result, the self-healing substance has a function of strengthening the muscles inside the subcutaneous layer. Using this function, so-called catgut-embedding therapy and pharmaco-thread injecting therapy have been developed.

The pharmaco-thread injecting therapy is a treatment that injects harmless threads (e.g., surgical absorbable sutures) into spots for acupuncture, painful spots, wrinkled or sagged spots, etc. of the human body through an injection kit. When a needle is inserted into the human body, the thread is injected into the subcutaneous layer along the needle, and when the needle is pulled out, the injected thread is separated from the needle and remains in the human body. This therapy has advantages such as simplification of procedure and less burden on the patient in comparison with the catgut-embedding therapy that requires the incision of the skin, the insertion of the thread, and suturing.

However, since the thread injected into the body through a conventional injection kit is a thin absorbable suture thread, the thread placed in the subcutaneous tissue has a small surface area and is melted after about six months. Therefore, the amount of generated self-healing substances is not sufficient. In addition, the thread is often broken or weakened due to a sharp tip of the needle in a process of being injected into the human body.

In order to solve the above problems, Korean Patent No. 10-1748755 (hereinafter referred to as one prior art) discloses an apparatus for inserting a medical thread composed of an absorbable suture thread and a gold thread. This thread can be used for a long time while increasing the amount of self-healing substances generated thereby. Further, a needle has a thread guide groove at the tip thereof, so that it is possible to prevent the medical thread from being broken or weakened when the needle is inserted into the human body.

FIG. 1 is an exploded view showing an apparatus for inserting a medical thread according to one prior art, and FIG. 2A is a partially cross-sectional view showing the apparatus shown in FIG. 1.

As shown in FIGS. 1 and 2A, a conventional medical thread inserting apparatus 100 includes an injection needle 110, a needle holder 120, a medical thread 130, and a cover 140. The injection needle 110 has an inclined portion 112 at one end thereof and also has a hollow portion (not shown) formed therein from the inclined portion 112 in the longitudinal direction. The hollow portion allows the injection needle 110 to be easily inserted into the human body. The needle holder 120 is formed of metal or synthetic resin and mounted on the other end of the injection needle 110. The medical thread 130 is formed of an absorbable suture thread 132 and a gold thread 134. A part of the absorbable suture thread 132 is inserted into the hollow portion (not shown), and the other part is disposed outside the injection needle 110. The gold thread 134 fixedly supports the absorbable suture thread 132 to the injection needle 110. The cover 140 protects the injection needle 110 and the medical thread 130.

As shown in FIG. 2A, the absorbable suture thread 132 of the medical thread 130 is disposed along the longitudinal outer surface of the needle 110. In addition, the gold thread 134 may be configured to be spirally wound on the absorbable suture thread 132 in the longitudinal direction, or may be configured to form a twisted structure along with the absorbable suture thread 132.

FIG. 2B is a view showing a process of using the medical thread inserting apparatus shown in FIG. 1.

As shown in FIG. 2B, after the cover 140 of the medical thread inserting apparatus 100 is removed, the injection needle 110 is brought into close contact with a muscle part to be treated. Then, the needle holder 120 is pressed to insert the injection needle 110 provided with the medical thread 130 into the human body. When the injection needle 110 is inserted into the human body, the medical thread 130 provided in the injection needle 110 is also moved to an inserted position of the injection needle 110 into the human body. Thereafter, when the injection needle 110 is pull out from the human body, the medical thread 130 fixedly remains in the human body to generate self-healing substances.

As described above, the medical thread 130 injected into the human body through the injection needle 110 causes the self-healing substances to gather around the medical thread 130. Accordingly, the self-healing substances having a function of strengthening muscles improve the elasticity of wrinkled skin.

In addition, the gold thread 134 constituting the medical thread 130 injected into a damaged part of the human body acts as a foreign matter. Therefore, the gold thread 134 induces the self-healing substances to be collected in the damaged part and allows the damaged part to be healed faster. Normally, the gold thread is made of pure gold, has a very small diameter (e.g., 0.1 to 0.2 mm), and is sterilized for medicinal purposes. As well known in the art, the gold thread is used for a special acupuncture technique that injects the gold thread into the subcutaneous muscles of the adaptive acupuncture points or pressure points of the human body to prevent and treat diseases.

However, in the above-described medical thread inserting apparatus 100, the injection needle 110 should have the hollow portion (not shown) formed therein from the inclined portion 112 such that a part of the absorbable suture thread 132 and a part of the gold thread 134 are inserted into the injection needle 110. Since the injection needle 110 has a long cylindrical form having a very small diameter (e.g., about 1 to 1.5 mm) to be inserted into the skin of the human body, it is very difficult to form the hollow portion (not shown) inside the injection needle 110 in the longitudinal direction. Further, in case of having to use an ultrafine machining technique, the manufacturing cost of the injection needle 110 is greatly increased.

In addition, even if it is possible to form the hollow portion (not shown) in the injection needle 110, another problem that it is very difficult to insert a part of the absorbable suture thread 132 and a part of the gold thread 134 into the hollow portion having a very small diameter arises.

Further, since the above-described medical thread inserting apparatus 100 is designed to inject the medical thread 130 composed of the absorbable suture thread 132 and the gold thread 134, it is not suitable for an apparatus for injecting only the gold thread 134.

Meanwhile, according to another prior art, a dual suturing needle set having a gold thread for a hair loss treatment has been developed and used.

FIG. 3 is a view showing a dual suturing needle set having a gold thread for a hair loss treatment according to another prior art. This dual suturing needle set is disclosed in Korean Patent Application No. 10-2016-0010451, which was filed on Jan. 28, 2016 by the same inventors as those of this application and registered as Korean Patent No. 10-1696855 on Jan. 10, 2017.

As shown in FIG. 3, the dual suturing needle set for a hair loss treatment according to another prior art includes a suture thread 20, a first needle 10, and a second needle 30. The suture thread 20 is composed of a plurality of strands having a gold thread. One end of the suture thread 20 is inserted in the first needle 10, and the other end is inserted in the second needle 30. Each of the first and second needles 10 and 30 has a needle part 12 or 32 formed at one end thereof, and may have an installation groove 14 or 34 formed with a predetermined depth at the other end thereof to allow the suture thread 20 to be inserted. The first and second needles 10 and 20 may have different lengths and each may have a bent part 16 or 36 formed with a predetermined angle. Each of the bent parts 16 and 36 may be located adjacent to the inner side of the installation groove 14 or 34 of each the first and second needles 10 and 30.

The above-described dual suturing needle set uses the suture thread 20 in which a gold thread as a non-absorbable suture thread 24 is wound on the surface of an absorbable suture thread 22 at predetermined intervals, thereby promoting hair formation and development. Also, using a set of long and short bent-form needles engaged with both ends of the suture thread 20 achieves an advantage of easily performing a treatment. However, the following problems still remain.

As described above, in the suture thread 20, the gold thread, which is the non-absorbable suture thread 24, is wound on the surface of the absorbable suture thread 22 at predetermined intervals with one or more strands. In order to treat the absorbable suture thread 22 and the non-absorbable suture thread 24 as one suture thread, it is required to compress the ends of the suture thread 20 by applying heat and pressure such that the non-absorbable suture thread 24 having a relatively small diameter is attached to the absorbable suture thread 22 having a relatively large diameter.

Further, a compressed part 26 is required to allow the ends of the suture thread 20 to be easily inserted into the installation grooves 14 and 34 of the first and second needles 10 and 30, respectively. Therefore, it is not easy to manufacture the suture thread itself, and also the manufacturing cost of the dual suturing needle set is increased.

In case of the above-described dual suturing needle set, a process of inserting and withdrawing the first needle 10 having a greater length into and from the biological tissue of the treatment area is repeated to suture the biological tissue of the treatment area. Then, the second needle 30 having a smaller length is withdrawn through a hole from which the first needle 10 is withdrawn, and a knot is inserted into the hole to complete the treatment. Therefore, this dual suturing needle set not only has a drawback of requiring two needles 10 and 30, but also causes a complicated and difficult operation including withdrawing the first needle 10 through a hole, then withdrawing the second needle 30 through the same hole, forming a knot, and inserting the knot into the hole.

Accordingly, a new technique to solve the above-described problems is required.

SUMMARY

In order to solve the above-described problems, the present disclosure provides a suturing needle capable of accurately and easily injecting a gold thread into a treatment area of scalp for a hair loss treatment and preventing the injected gold thread from separating from the treatment area.

According to one embodiment of the present disclosure, a suturing needle for injecting a gold thread may comprise a needle body having a sharpened tip part at an upper end thereof; an upper groove provided on the sharpened tip part to hold the gold thread therein; a lower groove provided near a lower end of the needle body to be opposite to the upper groove; and a handle part detachably combined with the lower end of the needle body.

According to another embodiment of the present disclosure, a suturing needle for injecting a gold thread may comprise a needle body having a sharpened tip part at an upper end thereof, the sharpened tip part having a flat upper surface; an upper groove provided on the flat upper surface of the sharpened tip part to hold the gold thread therein; a lower groove provided near a lower end of the needle body, the lower groove formed in a direction parallel with the upper groove; and a handle part detachably combined with the lower end of the needle body, wherein the lower groove includes one or both of first and second lower grooves which are formed on both sides of the needle body.

The suturing needle according to embodiments of the present disclosure has a variety of advantages over prior art. First, because the gold thread is not inserted into the needle body, there is no need to form a hollow portion in the needle body in the longitudinal direction. Second, this allows the suturing needle to be manufactured more simply with remarkably reduced cost and time. Third, contrary to prior art having to insert a part of the gold thread into the needle body or use two needles, the gold thread is used in a state of being hooked into the upper and lower grooves and of the needle body. This results in an easier and simpler use of the suturing needle. Finally, since it is possible to simultaneously inject two gold threads into the subject's scalp or skin, a treatment time can be shortened.

DETAILED DESCRIPTION

Hereinafter, the present disclosure will be described in detail with reference to the accompanying drawings.

Figure 1:
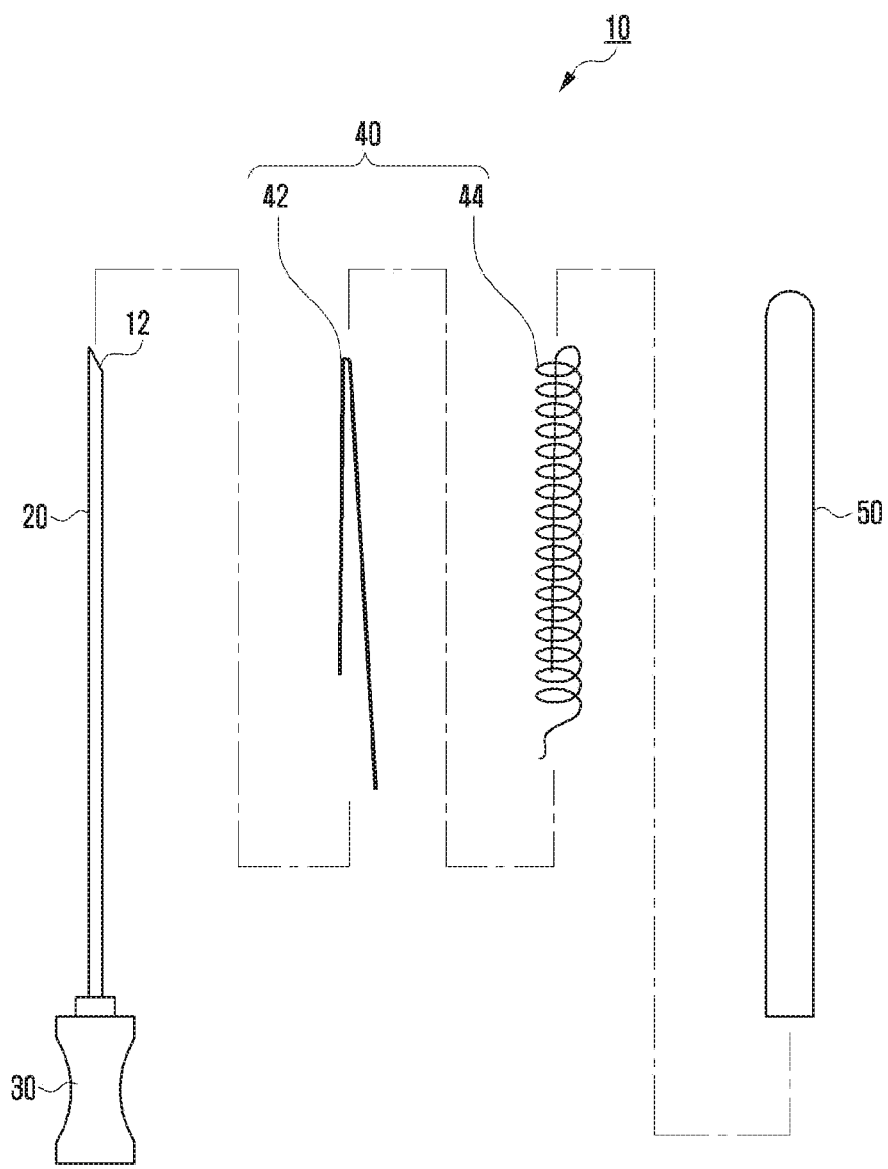
FIG. 1 is an exploded view showing an apparatus for inserting a medical thread according to one prior art.
Figure 2A:
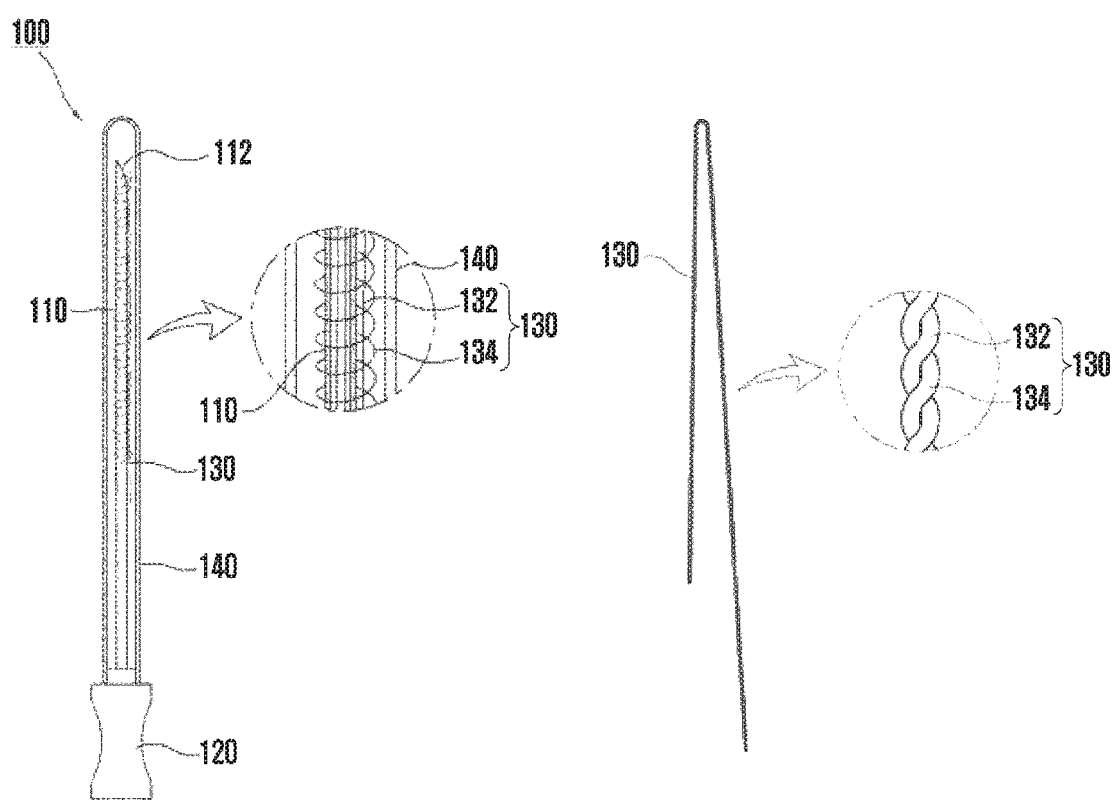
FIG. 2A is a partially cross-sectional view showing the apparatus shown in FIG. 1.
Figure 2B:
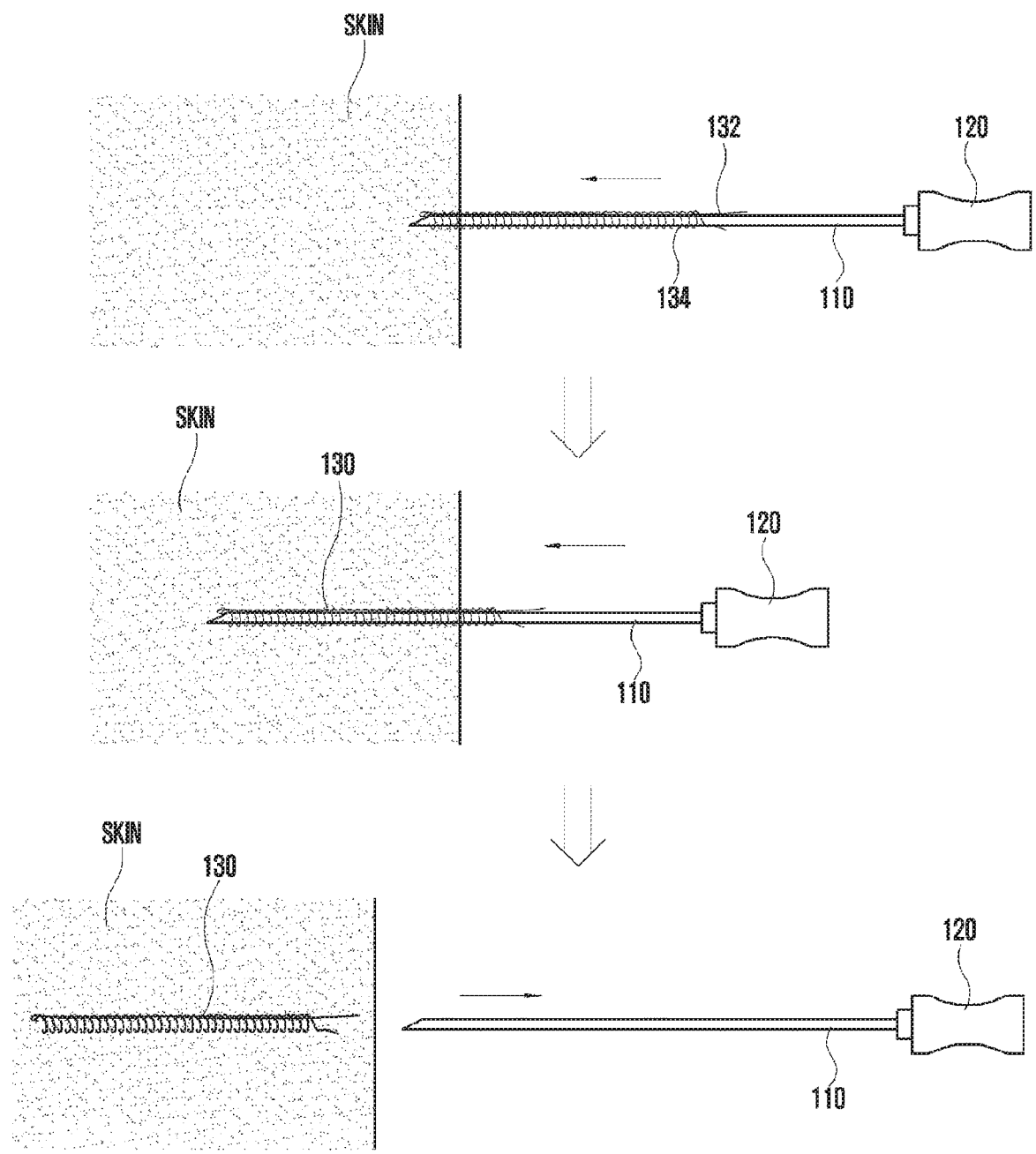
FIG. 2B is a view showing a process of using the medical thread inserting apparatus shown in FIG. 1.
Figure 3:
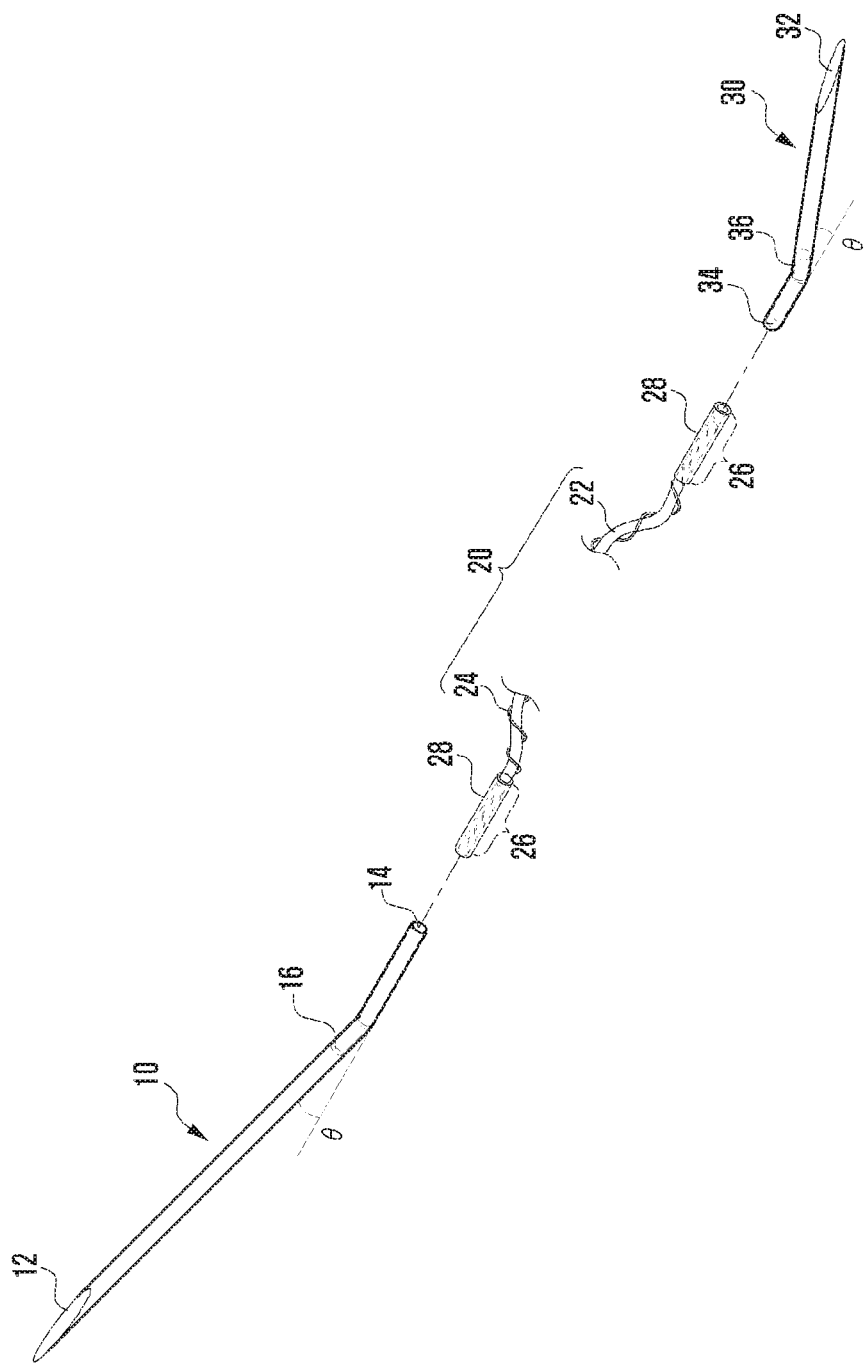
FIG. 3 is a view showing a dual suturing needle set having a gold thread for a hair loss treatment according to another prior art.
Figure 4:
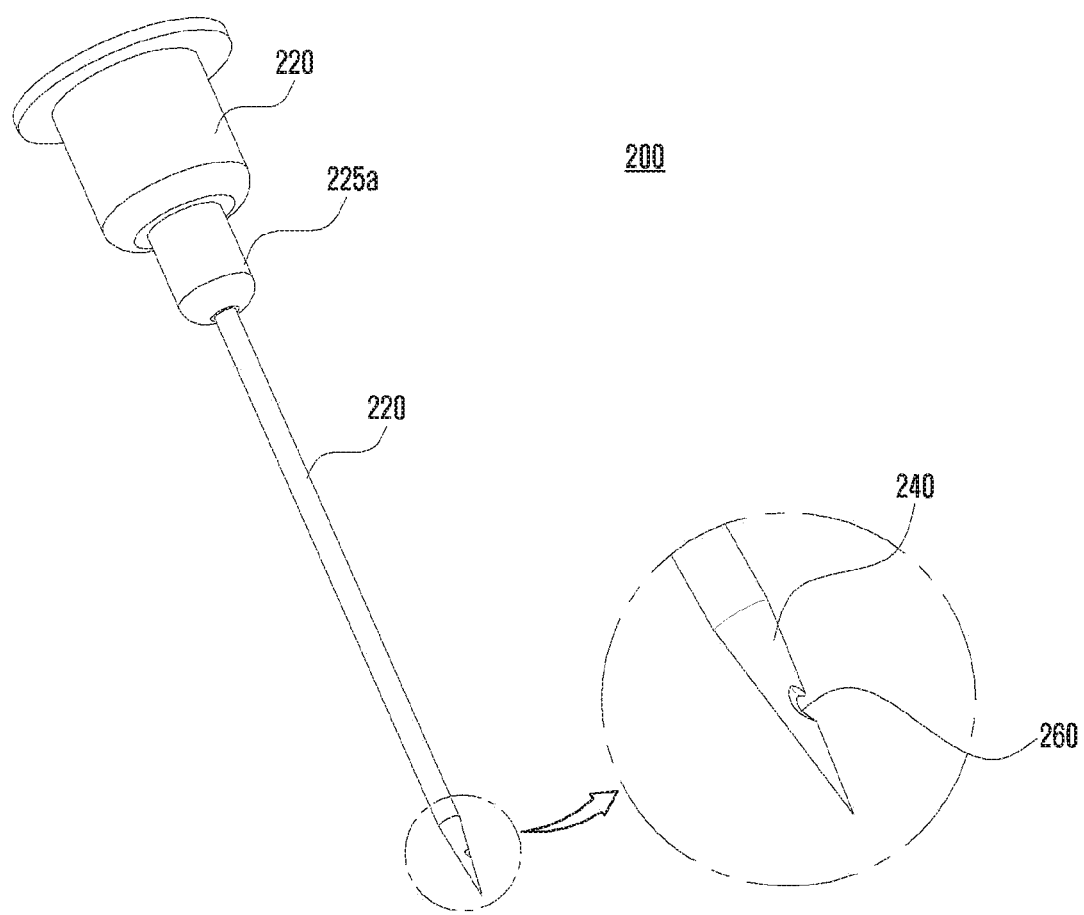
FIG. 4 is a perspective view showing a suturing needle for injecting a gold thread according to a first embodiment of the present disclosure.
Figure 5:
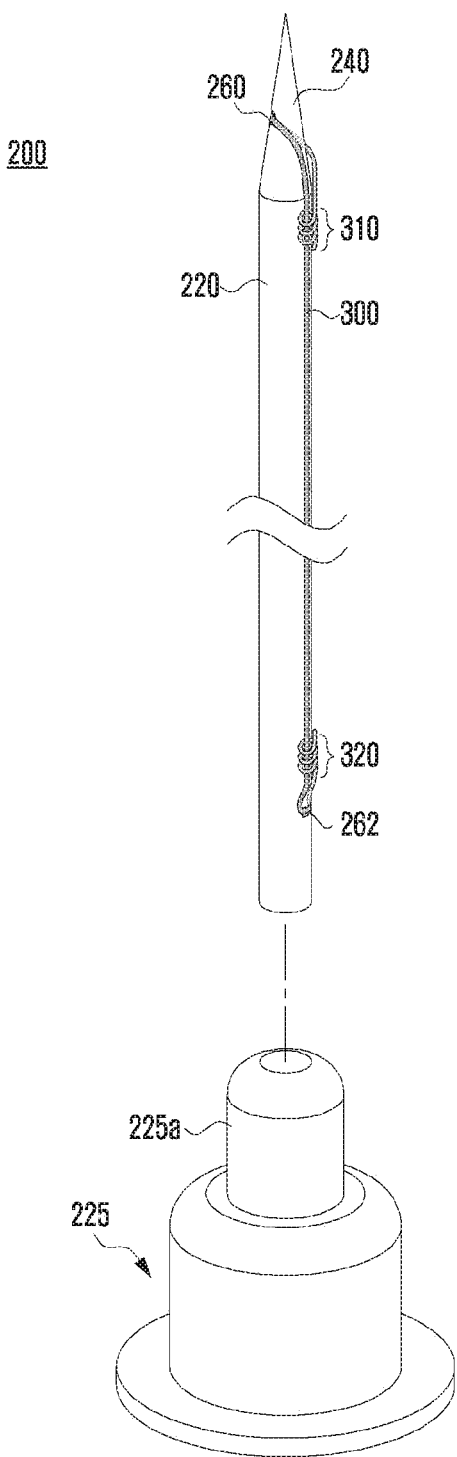
FIG. 5 is a perspective view showing a state in which a gold thread is attached to the suturing needle shown in FIG. 4 and a handle part is separated from a lower end of a needle body.
Figure 6:
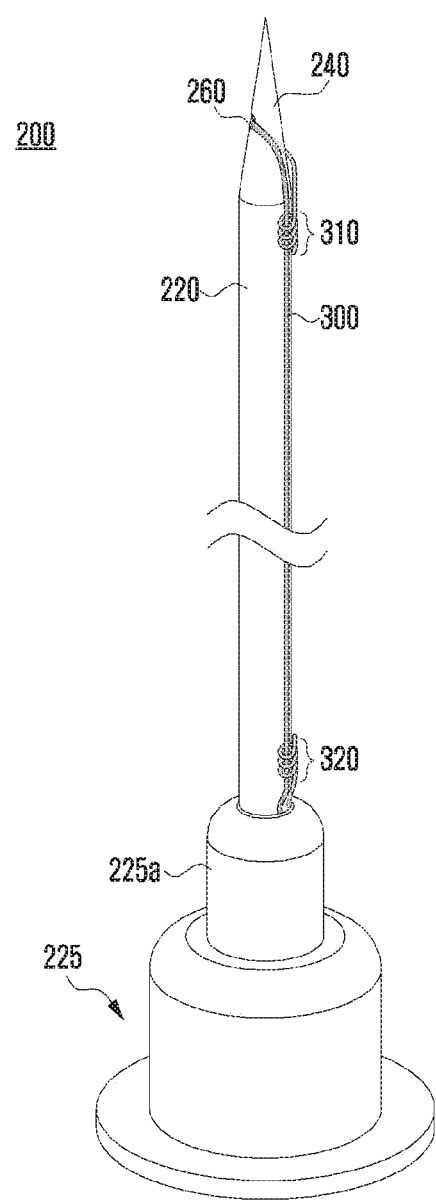
FIG. 6 is a perspective view showing a state in which a gold thread is attached to the suturing needle shown in FIG. 4 and a handle part is combined with a lower end of a needle body.

FIG. 4 is a perspective view showing a suturing needle for injecting a gold thread according to a first embodiment of the present disclosure. FIG. 5 is a perspective view showing a state in which a gold thread is attached to the suturing needle shown in FIG. 4 and a handle part is separated from a lower end of a needle body. FIG. 6 is a perspective view showing a state in which a gold thread is attached to the suturing needle shown in FIG. 4 and a handle part is combined with a lower end of a needle body.

As shown in FIGS. 4 to 6, a suturing needle 200 for injecting a gold thread according to the first embodiment of the present disclosure includes a needle body 220 having a sharpened tip part 240 at one end (i.e., upper end) thereof. In addition, the suturing needle 200 includes an upper groove 260 which is provided on the sharpened tip part 240 to hold a gold thread 300 therein, and a lower groove 262 which is provided near the other end (i.e., lower end) of the needle body 220 to be opposite to the upper groove 260. Also, the suturing needle 200 includes a handle part 225 which is detachably combined with the lower end of the needle body 220.

An upper portion of the gold thread 300 forms an upper twisted portion 310 such that the gold thread 300 is inserted and hooked into the upper groove 260. Similarly, a lower portion of the gold thread 300 forms a lower twisted portion 320 such that the gold thread 300 is inserted and hooked into the lower groove 262. Each of the upper and lower twisted portions 310 and 320 may be formed before or after the gold thread 300 is hooked into the upper and lower grooves 260 and 262.

The sharpened tip part 240 may have, for example, a conical shape as shown. This is, however, exemplary only and not to be construed as a limitation.

As shown in FIG. 4, the upper groove 260 is formed widthwise on one side of the sharpened tip part 240 and may have the form of a narrow trench which is dug downwardly, namely, in a direction from the upper groove 260 to the lower groove 262, such that the gold thread 300 can be easily separated from the upper groove 260 when the suturing needle 200 inserted into a treatment position of the human body is pull out.

Meanwhile, the handle part 225 may be detachably combined with the lower end of the needle body 220. For this, the handle part 225 may have a fastening protrusion 225a which is detachably combined with the lower end of the needle body 220. As shown in FIG. 6, the handle part 225 or the fastening protrusion 225a may cover the lower groove 262 when combined with the lower end of the needle body 220. This is, however, exemplary only. Alternatively, the handle part 225 or the fastening protrusion 225a may not cover the lower groove 262 even after combined with the lower end of the needle body 220. In addition, the fastening protrusion 225a is optional. In a certain embodiment, the handle part 225 only may be detachably combined with the needle body 220. The handle part 225 and/or the fastening protrusion 225a may be formed of, for example, an elastic material such as rubber, polyurethane, elastic plastic, or the like.

As described above, in the first embodiment, the lower groove 262 is provided near the lower end of the needle body 220 to hold the gold thread 300 therein. However, as will be appreciated by those skilled in the art, a specific mark (not shown) for gripping the gold thread may be provided instead of the lower groove 262. In this alternative case, an operator may use the suturing needle 200 while holding the lower twisted portion 320 positioned on the mark (not shown) for gripping the gold thread 300.

Hereinafter, a detailed method of using the suturing needle 200 according to the first embodiment of the present disclosure will be described.

At the outset, the upper and lower twisted portions 310 and 320 are formed respectively at upper and lower portions of the gold thread 300 having a certain length such that the gold thread 300 is hooked into the upper and lower grooves 260 and 262.

Next, the upper twisted portion 310 is hooked into the upper groove 260, and the lower twisted portion 320 is hooked into the lower groove 262. When the gripping mark (not shown) is provided instead of the lower groove 262 as described above, the lower twisted portion 320 positioned on the mark is held by the operator.

Then, the handle part 225 or the fastening protrusion 225a is combined with the lower end of the needle body 220. At this time, the handle part 225 or the fastening protrusion 225a may or may not cover the lower groove 262.

Then, the operator grips the handle part 225 of the suturing needle 200 and inserts the sharpened tip part 240 of the suturing needle 200 into a treatment position of a subject's skin (e.g., scalp). At this time, the upper portion of the gold thread 300 maintains a hooked state in the upper groove 260, and the lower portion of the gold thread 300 maintains a hooked state in the lower groove 262. In case where the gripping mark (not shown) is provided instead of the lower groove 262, the operator continuously holds the lower twisted portion 320 positioned on the mark.

Thereafter, using the lower twisted portion 320, the operator releases the hooked state of the gold thread 300 in the lower groove 262. If the handle part 225 or the fastening protrusion 225a covers the lower groove 262, the handle part 225 or the fastening protrusion 225a may be moved backward so as to expose the lower groove 262 and then release the hooked state of the gold thread 300 in the lower groove 262.

Then, the operator pulls out the needle body 220 from the treatment position while pushing the scalp or skin where the suturing needle 200 is positioned. Therefore, the upper portion of the gold thread 300 is released from the upper groove 260 and fixed to the treatment position.

The above-described suturing needle 200 according to the first embodiment of the present disclosure can be used for a gold lifting treatment that injects the gold thread 300 into the SMAS (Superficial Musculoaponeurotic System) layer under the subject's scalp. In this case, the gold thread 300 induces a foreign matter reaction in the human body of the subject, thereby producing natural collagen and inducing capillary vessel formation in the skin. Particularly, the produced collagen is not injected from the outside forcefully but is produced by itself in the skin of the human body. Therefore, this has no side effects on wrinkle removal, skin elasticity provision, and skin tone improvement, and has an advantage of long effect duration.

Figure 7:
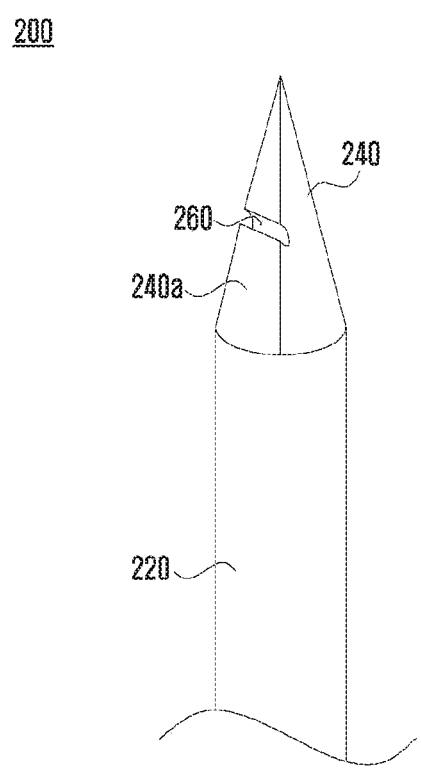
FIG. 7 is a perspective view showing a variation of a sharpened tip part of the suturing needle shown in FIG. 4.

FIG. 7 is a perspective view showing a variation of a sharpened tip part of the suturing needle shown in FIG. 4.

Referring to FIG. 7, the above-described suturing needle 200 according to the first embodiment of the present disclosure may have a variation of the sharpened tip part 240. That is, a part of the sharpened tip part 240 having a conical shape as shown in FIG. 4 may be implemented to have a triangular plane 240a. In this case, the upper groove 260 may be provided on the triangular plane 240a.

Figure 8:
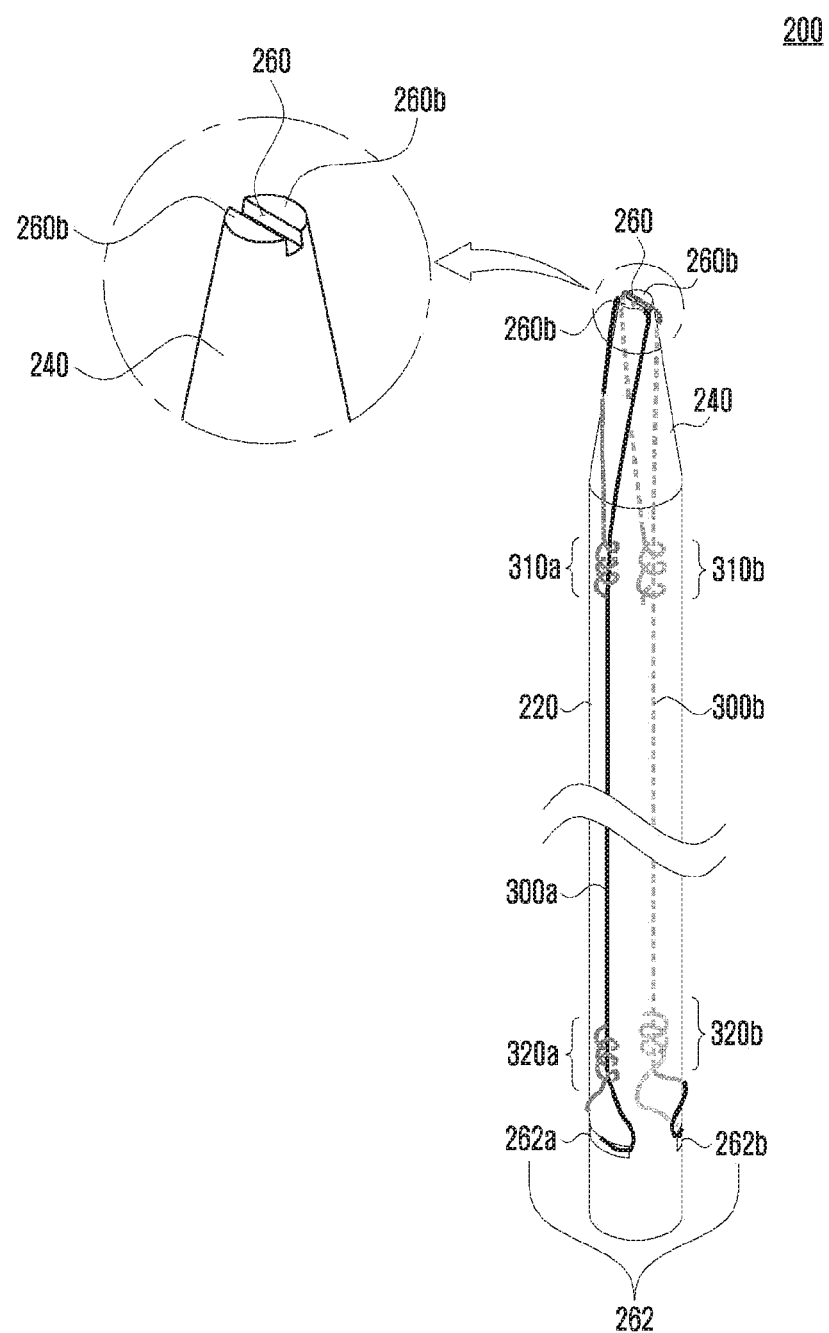
FIG. 8 is a perspective view showing a suturing needle for injecting a gold thread according to a second embodiment of the present disclosure.

FIG. 8 is a perspective view showing a suturing needle for injecting a gold thread according to a second embodiment of the present disclosure.

As shown in FIG. 8, a suturing needle 200 for injecting a gold thread according to the second embodiment of the present disclosure includes a needle body 220 having a sharpened tip part 240 at one end (i.e., upper end) thereof. The sharpened tip part 240 has a flat upper surface 240b. In addition, the suturing needle 200 includes an upper groove 260 which is provided on the flat upper surface 240b of the sharpened tip part 240 to hold a gold thread 300 therein, and a lower groove 262 which is provided near the other end (i.e., lower end) of the needle body 220. The upper and lower grooves 260 and 262 are formed in a direction parallel with each other. Also, the suturing needle 200 includes a handle part 225 which is detachably combined with the lower end of the needle body 220. The lower groove 262 may include one or both of first and second lower grooves 262a and 262b which are formed on both sides of the needle body 220.

In the suturing needle 200 according to the second embodiment, the upper groove 260 is formed on the flat upper surface 240b of the sharpened tip part 240 which is provided at the upper end of the needle body 220. In addition, one or both of the first and second lower grooves 262a and 262b is or are formed on the side(s) of the needle body 220 near the lower end of the needle body 220. Excepting these features, the suturing needle according to the second embodiment is substantially the same as the above-described suturing needle according to the first embodiment.

In the suturing needle 200 according to the second embodiment, two gold threads, i.e., first and second gold threads 300a and 300b may be used. An upper portion of the first gold thread 300a forms a first upper twisted portion 310a such that the first gold thread 300a is inserted and hooked into the upper groove 260. Also, an upper portion of the second gold thread 300b forms a second upper twisted portion 310b such that the second gold thread 300b is inserted and hooked into the upper groove 260. In addition, a lower portion of the first gold thread 300a forms a first lower twisted portion 320a such that the first gold thread 300a is inserted and hooked into the first lower groove 262a.

Also, a lower portion of the second gold thread 300b forms a second lower twisted portion 320b such that the second gold thread 300b is inserted and hooked into the second lower groove 262b. However, as will be appreciated by those skilled in the art, only one or all of the first and second gold threads 300a and 300b may be selectively used.

In addition, as earlier described in the first embodiment, a specific mark (not shown) for gripping the gold thread may be provided instead of each of the first and second lower grooves 262a and 262b.

Meanwhile, the suturing needle 200 according to embodiments of the present disclosure can be used for injecting the gold thread 300 into the skin of the subject as well as the scalp. That is, the suturing needle 200 according to embodiments of the present disclosure is not limited to the purpose of a hair loss treatment.

The suturing needle 200 according to embodiments of the present disclosure has a variety of advantages over prior art. First, because the gold thread 300 is not inserted into the needle body 220, there is no need to form a hollow portion in the needle body 220 in the longitudinal direction. Second, this allows the suturing needle 200 to be manufactured more simply with remarkably reduced cost and time. Third, contrary to prior art having to insert a part of the gold thread 300 into the needle body 220 or use two needles, the gold thread 300 is used in a state of being hooked into the upper and lower grooves 260 and 262 of the needle body 220. This results in an easier and simpler use of the suturing needle 200. Finally, since it is possible to simultaneously inject two gold threads 300a and 300b into the subject's scalp or skin, a treatment time can be shortened.

While the present disclosure has been particularly shown and described with reference to exemplary embodiments thereof, it is clearly understood that the same is by way of illustration and example only and is not to be taken in conjunction with the present disclosure. It will be understood by those skilled in the art that various changes in form and details may be made therein without departing from the subject matter and scope of the present disclosure.

What is claimed is:

1. A suturing needle for injecting a gold thread, comprising:
   a needle body having a sharpened tip part at a distal end thereof;
   an upper groove provided on the sharpened tip part to hold the gold thread therein;
   a thread locator means, for positioning an end of the gold thread on the needle body, provided at a proximal end of the needle body; and
   a handle part detachably combined with the lower end of the needle body, wherein
   the upper groove and the thread locator means are disposed on different sides of the needle body, the different sides opposite to one another along a central longitudinal axis of the needle body, and
   the sharpened tip part has a conical shape or has partially a triangular plane.

2. The suturing needle of claim 1, wherein the thread locator means includes a specific mark provided on the needle body.

3. The suturing needle of claim 1, wherein the handle part has a fastening protrusion detachably combined with the lower end of the needle body.

4. The suturing needle of claim 3, wherein the handle part or the fastening protrusion is formed of an elastic material.

5. A kit comprising:
   a gold thread; and a suturing needle for injecting the gold thread, the suturing needle including:
  a needle body having a sharpened tip part at a distal end thereof;
  an upper groove provided on the sharpened tip part to hold the gold thread therein;
  a thread locator means, for positioning an end of the gold thread on the needle body, provided at a proximal end of the needle body; and
  a handle part detachably combined with the lower end of the needle body, wherein
  the upper groove and the thread locator means are disposed on different sides of the needle body, the different sides opposite to one another along a central longitudinal axis of the needle body, and
  the sharpened tip part has a conical shape or has partially a triangular plane.

6. The kit of claim 5, wherein:
an upper portion of the gold thread forms an upper twisted portion such that the gold thread is inserted and hooked into the upper groove, and
a lower portion of the gold thread forms a lower twisted portion such that the gold thread is inserted and hooked into a lower groove provided as the thread locator means.

7. The kit of claim 6, wherein each of the upper and lower twisted portions is formed before or after the gold thread is hooked into each of the upper and lower grooves.

8. The suturing needle of claim 1, wherein the thread locator means includes a lower groove provided on the needle body.

* * * * *